US00PP27341P3

(12) United States Plant Patent
Van Swieten

(10) Patent No.: US PP27,341 P3
(45) Date of Patent: Nov. 1, 2016

(54) ***PHALAENOPSIS* ORCHID PLANT NAMED 'PHALDASYH'**

(50) Latin Name: ***Phalaenopsis* hybrid**
Varietal Denomination: PHALDASYH

(71) Applicant: ANTHURA B.V., Bleiswijk (NL)

(72) Inventor: Martinus Nicolaas Gerardus Van Swieten, The Hague (NL)

(73) Assignee: ANTHURA B.V., Bleiswijk (NL)

( * ) Notice: Subject to any disclaimer, the term of this patent is extended or adjusted under 35 U.S.C. 154(b) by 95 days.

(21) Appl. No.: 14/121,864

(22) Filed: Oct. 28, 2014

(65) Prior Publication Data

US 2016/0120088 P1 Apr. 28, 2016

(51) Int. Cl.
*A01H 5/02* (2006.01)

(52) U.S. Cl.
USPC ..... Plt./311

(58) Field of Classification Search
USPC ..... Plt./311
See application file for complete search history.

(56) References Cited

PUBLICATIONS

Upov Pluto Plant Variety Databse Mar. 24, 2016 retrieved on Mar. 29, 2016, retrieved from the Internet at <http://www.upov.int/pluto/en/index.jsp> one page.*
Anthura unlimited varieties Phalaenopsis Pot plant culture, retrieved on Mar. 30, 2016, retrieved from the Internet at <http://www.grenethplants.nl/images/brochures/PHALAENOPSIS.pdf> pp. 1, 10, 34, 37 and 50-51.*
EU Community Plant Variety Rights, Official Gazette, 3.2014, Jun. 15, 2014, pp. 37 and 56.
EU Community Plant Variety Rights, Official Gazette, 3.2015, Jun. 15, 2015, p. 81.
EU Community Plant Variety Rights application No. 20141138, filed Apr. 25, 2014, 7 pp.

* cited by examiner

*Primary Examiner* — June Hwu
(74) *Attorney, Agent, or Firm* — Jondle & Associates, P.C.

(57) ABSTRACT

A new and distinct variety of *Phalaenopsis* plant named 'PHALDASYH', particularly characterized by yellowish-white flowers with purple shade and dark purple spots, 2 peduncles, inflorescence that is long and sturdy, leaves that are between oblong and lanceolate shape, and propagated by tissue culture is disclosed.

3 Drawing Sheets

Genus and species: *Phalaenopsis* hybrid.
Variety denomination: 'PHALDASYH'.

BACKGROUND OF THE NEW PLANT

The present invention comprises a new and distinct cultivar of *Phalaenopsis* plant, botanically known as *Phalaenopsis* of the Orchidaceae family, and hereinafter referred to by the cultivar name 'PHALDASYH'.

*Phalaenopsis* comprises a genus of about 60 species of herbaceous perennials many of which, or the hybrids thereof, are suitable for cultivar in the home or greenhouse. *Phalaenopsis* is predominantly epiphytic or rock dwelling, and is native to tropical Asia, the Malay Archipelago, and Oceania. The species typically has 2-ranked, fleshy, oblong or elliptic leaves affixed to a short central stem (monopodial growth), which vary in size from 12 to 20 cm to over 60 cm. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes or panicle, often with many showy flowers which open in succession beginning with the lowermost. The flowers possess three sepals and three petals; the lateral ones being alike. The lowermost petals, called the labellum, is three-lobed and is often more brightly-colored than the other flower segments. Flower colors include various shades of pink, white, yellow, and red-brown.

*Phalaenopsis* orchids are typically propagated from seeds. Asexual propagation of *Phalaenopsis* is often done from off-shoots which arise from the lower bracts of the inflorescence. The resulting plants are detached from the mother plants and may be planted in a suitable substrate.

The new *Phalaenopsis* 'PHALDASYH' is particularly characterized by its attractive and unique yellowish-white flowers with purple shade and dark purple spots, economical propagation by tissue culture, rapid growth, and a plant dimension suitable for packaging and shipping to the market.

'PHALDASYH' is a product of a planned breeding program conducted in Bleiswijk, The Netherlands.

The new *Phalaenopsis* 'PHALDASYH' originated from a cross made in May 2005 in Bleiswijk, The Netherlands. The female parent is a yellow flecked *Phalaenopsis* pot plant named '00001-5017' (unpatented), while the male parent is a pink *Phalaenopsis* pot plant named '22791-0004' (unpatented). A single plant was selected in June 2008 and has been asexually reproduced repeatedly by meristem tissue culture in Bleiswijk, The Netherlands over a 3-year period. The new variety has been found to retain its distinctive characteristics through successive asexual propagations.

Asexual reproduction of 'PHALDASYH' by meristem tissue culture was first performed in July 2011 in Bleiswijk, The Netherlands and has demonstrated that the new cultivar is firmly fixed and retained through successive generations of asexual reproduction.

Plant Breeder's Rights for this variety have been applied for in Europe on Apr. 25, 2014. 'PHALDASYH' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands.

1) Yellowish-white flowers with purple shade and dark purple spots;
2) 2 peduncles;
3) Inflorescence is long and sturdy;
4) The shape of the leaves is between oblong and lanceolate; and
5) Plants are propagated by tissue culture.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs are of a 50-week old plant grown in a greenhouse in Bleiswijk, The Netherlands in May 2014.

DESCRIPTION OF THE NEW VARIETY

Figure 1:
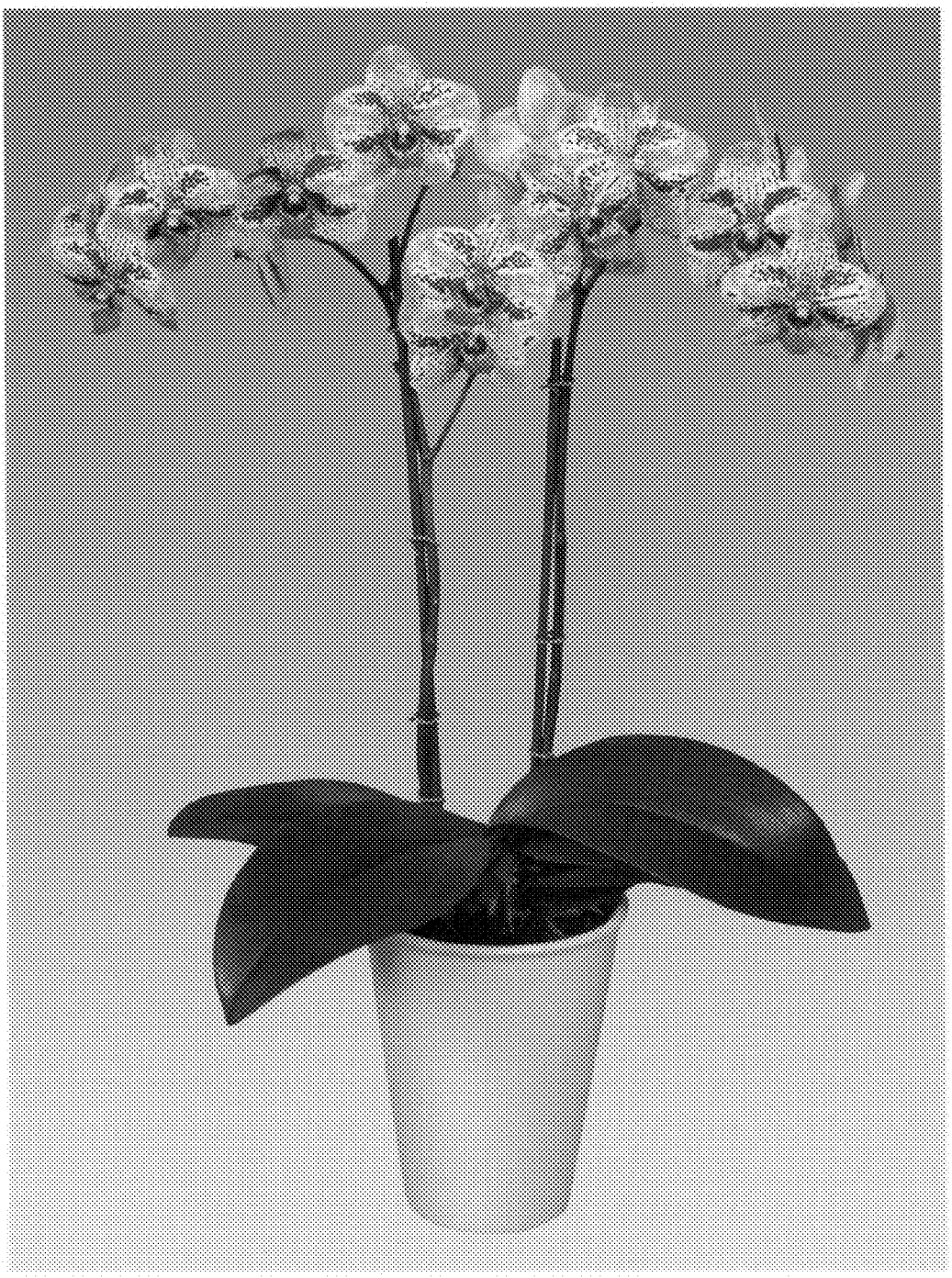
FIG. 1 shows the overall plant habit, including blooms, buds and foliage of 'PHALDASYH'.
Figure 2:
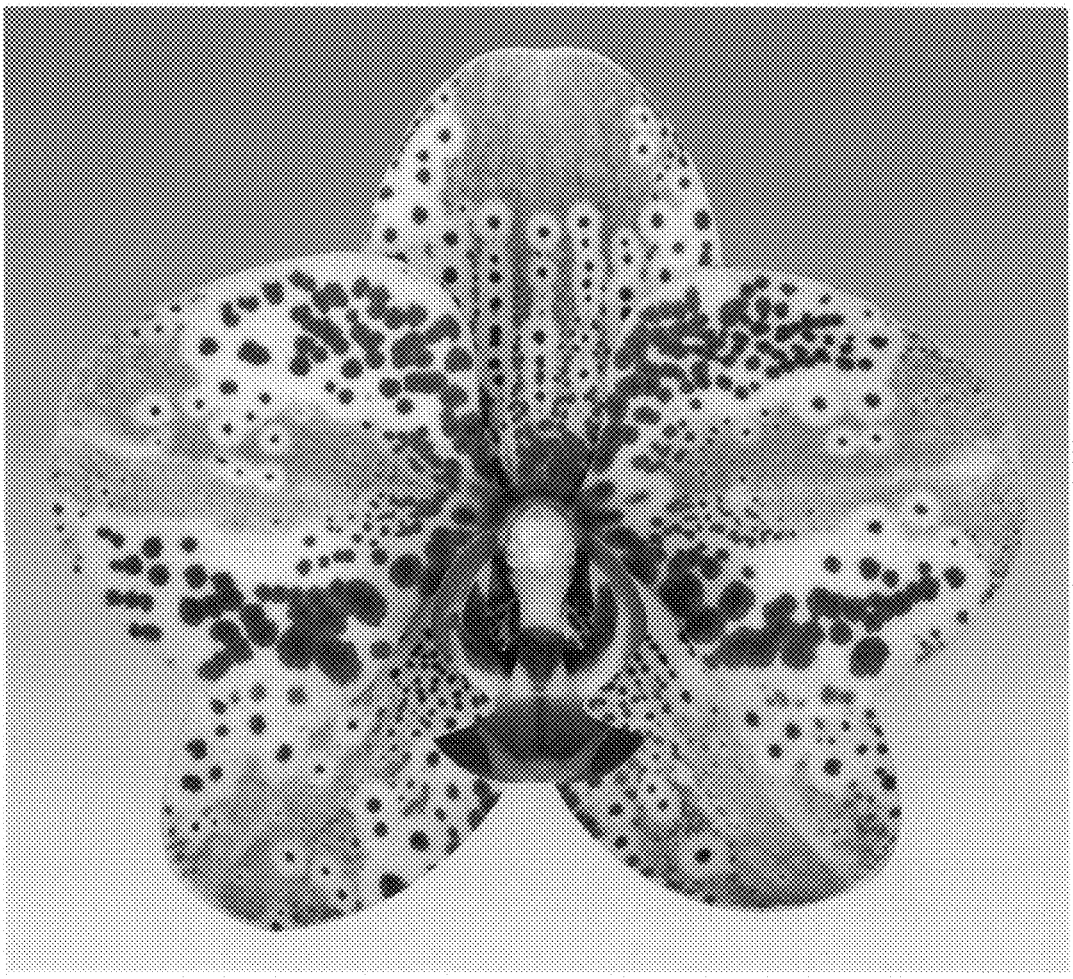
FIG. 2 shows a close-up of a flower of 'PHALDASYH'.
Figure 3:
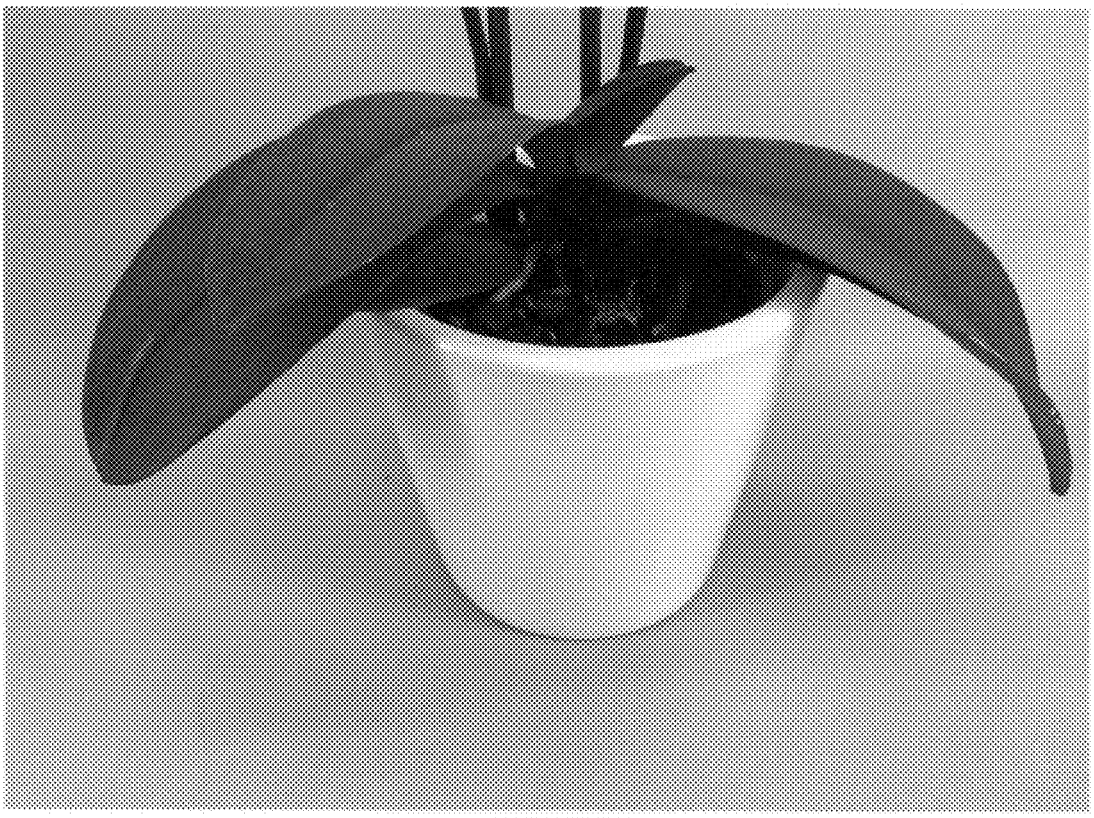
FIG. 3 shows a close-up of the leaves of 'PHALDASYH'.

The following detailed description sets forth the distinctive characteristics of 'PHALDASYH'. The data which define these characteristics were collected from asexual reproductions carried out in Bleiswijk, The Netherlands. The plant history was taken on 50-week old plants which were planted from tissue culture in 12 centimeter pots and grown in a greenhouse between 27° C. to 29° C. for 30 weeks, continued by a cooling period of 8 weeks between 18° C. to 20° C. and 12 weeks in a greenhouse of 21° C. Observations were made in May 2014. Color readings were taken under 4-6000 lux natural light in the greenhouse. Color references are primarily to The R.H.S. Colour Chart of The Royal Horticultural Society of London (R.H.S.) (1995 and 2015).

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALDASYH'.

Parentage:

*Female parent*.—*Phalaenopsis* cultivar '00001-5017' (unpatented).

*Male parent*.—*Phalaenopsis* cultivar '22791-0004' (unpatented).

Propagation:

*Type*.—Meristem tissue culture.

Plant:

*Crop time* (*time to produce a finished flowering plant*).—48 to 50 weeks for a 12 cm pot.

*Growth habit of inflorescence*.—Standard, green leaves and raceme to panicle.

*Height* (*including pot, including inflorescence*).—58.0 cm to 68.0 cm.

*Width* (*measured from leaf tips*).—32.0 cm to 36.0 cm.

*Vigor*.—Strong.

Roots:

*Root description*.—Grey-green-colored roots with branching lateral roots having grey-green-colored root tips.

Leaves:

*Mature leaves*.—Quantity per plant: 7 to 8 leaves are produced before flowering. Length (fully expanded): 14.0 cm to 19.0 cm. Width: 6.5 cm to 8.5 cm. Shape: Between oblong and lanceolate. Apex: Unequal mucronate. Leaf blade angle with the petiole: Between 5 degrees and 20 degrees. Leaf margin: Entire. Color: Upper surface: RHS 146A, with edge of the leaf 187A. Lower surface: RHS 147B and 187B. Texture: Smooth. Thickness: 2.7 mm to 3.1 mm. Venation: Pattern: Parallel. Color of the midvein: Upper surface: RHS 187A. Lower surface: RHS 187B.

Peduncle:

*Quantity per plant*.—2.

*Number of flowers per peduncle*.—7 to 12.

*Length*.—58.0 cm to 63.0 cm.

*Diameter*.—4.4 mm to 4.7 mm.

*Strength*.—Strong.

*Aspect*.—Upright.

*Texture*.—Smooth.

*Color*.—Green (RHS 146B) with brown bracts and anthocyanin (RHS 183B) towards the lower section of the peduncle.

*Internode length*.—40.0 mm to 50.0 mm.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 210.0 mm to 260.0 mm. Diameter of the peduncle at the inflorescence: 3.4 mm to 4.2 mm.

*Flowering time*.—First flowers can be expected 10 to 11 months after planting in a 12 cm pot.

*Flower bud*.—Length: 2.3 cm to 2.5 cm. Width: 1.8 cm to 2.0 cm. Shape: Egg shaped. Color: Light green (RHS 145C) and diluted greyish purple (RHS N77A).

*Flower*.—Height: 82.0 mm to 87.0 mm. Diameter: 84.0 mm to 89.0 mm. Depth of lip: 18.0 mm to 20.0 mm.

*Flower longevity*.—On the plant: 10 to 15 weeks.

*Fragrance*.—Absent.

*Petals*.—Note: The number and intensity of spots on the flower may vary depending on the temperature, with the number and intensity of the petal spots decreasing with warmer temperatures. Arrangement: Open. Shape: Semi-circular. Apex: Emarginate and asymmetric. Margin: Entire. Length (from base to tip): 38.0 mm to 40.0 mm. Width: 40.0 mm to 42.0 mm. Color (when newly opened): Upper surface: Main color: Purple shade (RHS 78B) and dark purple spots (RHS N79C). At the base: Light yellow green (RHS 150D). Lower surface: Main color: Purple shade (RHS N78D) and diluted purple spots (RHS N79B). At the base: Yellow-green (RHS 145D). Color (when fully opened): Upper surface: Main color: Purple shade (RHS 78B) and dark purple spots (RHS N79C). At the base: Yellowish white (RHS 155B). Lower surface: Main color: Purple shade (RHS 78B) and diluted purple spots (RHS N79C). At the base: Pale yellow-green (RHS 157B). Petal spots: Average number: Medium to many. Average size: Small to medium. Location: Along the sides and base of petals with few sporadic centrally.

*Dorsal sepal*.—Shape: Elliptic. Margin: Entire. Length (from base to tip): 42.0 mm to 45.0 mm. Width: 32.0 mm to 34.0 mm. Color (when fully opened): Upper surface: Main color: Purple shade (RHS 78B) and purple spots (RHS N79C). At the base: Yellowish white (RHS 155B). Lower surface: Main color: Purple shade (RHS 78B) and diluted purple spots (RHS N79B). At the base: Yellow-green (RHS 145C/D). Dorsal sepal spots: Average number: Medium to many. Average size: Small to medium. Location: Covering about ¾ of sepal.

*Lateral sepals*.—Shape: Ovate. Margin: Entire. Length (from base to tip): 40.0 mm to 43.0 mm. Width: 28.0 mm to 30.0 mm. Color (when fully opened): Upper surface: Main color: Purple shade (RHS 78B) and dark purple spots (RHS N79C). At the base: Yellowish white (RHS 155B). Lower surface: Main color: Purple (RHS N78D) and diluted purple spots (RHS N79B). At the base: Yellow-green (RHS 145C/D). Lateral sepal spots: Average number: Medium to many. Average size: Small to medium. Location: Covering about ½ to ¾ of the lateral sepal depending on the temperature during the flower bud development.

*Labellum* (*lip*).—Margin: The whole labellum is entire (lateral and apical lobes). Length: 17.0 mm to 19.0 mm. Width: 17.0 mm to 19.0 mm. Whiskers: Length: 0.3 cm to 0.5 cm. Color: Purple (RHS N78A).

*Lateral lobe*.—Length: 14.0 mm to 16.0 mm. Width: 8.0 mm to 10.0 mm. Shape: Type IV (as described in the International Union for the Protection of New Varieties of Plants (UPOV) Test Guidelines for *Phalaenopsis*). Color: Yellow (RHS 15A) at the base (towards the callus) with RHS 187A centrally and RHS 78A along the margin.

*Apical lobe*.—Length: 18.0 mm to 20.0 mm. Width: 16.0 mm to 18.0 mm. Shape: Rhombic. Color: Purple/red with RHS 60A at the base (towards the callus) and RHS 78A towards the whiskers.

*Callus*.—Height: Moderately raised; 0.5 cm to 0.6 cm. Length: 0.3 cm to 0.4 cm. Width: 0.4 cm to 0.5 cm. Color: Dark purple/red (RHS 187B). Pubescence: None.

*Pedicel*.—Length: 31.0 mm to 34.0 mm. Diameter: 2.6 mm to 3.0 mm.

Reproductive organs:

*Arrangement*.—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column*.—Length: 10.0 mm to 13.0 mm. Diameter: 5.5 mm to 6.0 mm. Color: Purple (RHS 78A).

*Pollinia*.—Quantity: 2. Size: 0.9 mm to 1.1 mm. Color: Light orange (RHS 23A).

*Ovary*.—Length: 7.0 mm to 9.0 mm. Diameter: 2.4 mm to 2.8 mm.

Disease, pest, and stress resistance: No specific resistance or susceptibility observed.

Temperature tolerance: Tolerant to a low temperature of 15° C. and a high temperature about 30° C.

COMPARISON WITH PARENTAL AND COMMERCIAL VARIETIES

'PHALDASYH' differs from female parent '00001-5017' (unpatented) in that 'PHALDASYH' has a flower that is yellowish-white with purple shade and dark purple spots, whereas '00001-5017' has a flower that is yellow flecked.

'PHALDASYH' differs from male parent '22791-0004' (unpatented) in that 'PHALDASYH' has a flower that is yellowish-white with purple shade and dark purple spots, whereas '22791-0004' has a flower that is evenly pink. Additionally, 'PHALDASYH' has a lateral lobe shape that is type IV and a callus that is dark purple/red, whereas '22791-0004' has a lateral lobe shape that is type V and a callus that is yellow.

'PHALDASYH' differs from commercial variety 'PHALFUMWIK' (unpatented) in that 'PHALDASYH' has a flower that is yellowish-white with purple shade and dark purple spots, whereas 'PHALFUMWIK' has a flower that is white with purple flecks. Additionally, 'PHALDASYH' has a type IV lateral lobe that is purple and yellow and a rhombic apical lobe, whereas 'PHALFUMWIK' has a type V lateral lobe that is white with darker purple flecks and a little bit of yellow on one side and a triangular apical lobe.

I claim:

1. A new and distinct variety of *Phalaenopsis* plant named 'PHALDASYH', substantially as described and illustrated herein.

* * * * *